United States Patent [19]

Rao et al.

[11] Patent Number: 5,345,017
[45] Date of Patent: Sep. 6, 1994

[54] PROCESS FOR REDUCING THE FLUORINE CONTENT OF HALOCARBONS

[75] Inventors: V. N. Mallikarjuna Rao; Steven H. Swearingen, both of Wilmington, Del.

[73] Assignee: E. I. Du Pont de Nemours and Company, Wilmington, Del.

[21] Appl. No.: 148,032

[22] Filed: Nov. 5, 1993

Related U.S. Application Data

[63] Continuation of Ser. No. 986,811, Dec. 8, 1992, abandoned.

[51] Int. Cl.$^5$ .................... C07C 17/34; C07C 19/08
[52] U.S. Cl. .................................. 570/227; 570/163; 570/170
[58] Field of Search .................... 570/227, 163, 170

[56] References Cited

U.S. PATENT DOCUMENTS

| | | |
|---|---|---|
| 3,193,587 | 7/1965 | Baranauckas et al. . |
| 3,541,165 | 11/1970 | Vecchio et al. . |
| 3,632,834 | 1/1972 | Christoph . |
| 3,754,043 | 8/1973 | Bjornson et al. . |
| 4,766,260 | 8/1988 | Manzer . |
| 4,902,838 | 2/1990 | Manzer et al. . |
| 5,036,036 | 7/1991 | Lerou . |
| 5,036,036 | 7/1991 | Lerou . |
| 5,132,473 | 7/1992 | Furutaka et al. ............... 570/123 |
| 5,171,899 | 12/1992 | Furutaka et al. . |

FOREIGN PATENT DOCUMENTS

| | | |
|---|---|---|
| 2025145 | 9/1990 | Canada . |
| 0514920 | 5/1990 | European Pat. Off. . |

OTHER PUBLICATIONS

Vecchio et al., *J. Fluorine Chemistry*, 4, 117–139, 1974.

*Primary Examiner*—alan Siegel

[57] ABSTRACT

The fluorine content of an acyclic saturated compound of the formula $C_nF_aX_b$ having at least one carbon with at least two fluorine substituents (wherein each X is independently selected from Cl and Br, and wherein n is 1 to 4, a is 2 to 10, b is 0 to 8, and a+b equals 2n+2) is reduced by reacting the acyclic saturated compound with HCl in the vapor phase at an elevated temperature in the presence of a catalyst, the mole ratio of HCl to the acyclic saturated compound being at least about 2:1.

20 Claims, No Drawings

PROCESS FOR REDUCING THE FLUORINE CONTENT OF HALOCARBONS

This is a continuation of application Ser. No. 07/986,811 filed Dec. 8, 1992, now abandoned.

FIELD OF THE INVENTION

This invention relates to halogen-substituted hydrocarbons containing fluorine and more particularly, to a process for reducing the fluorine content of fluorine-containing halocarbons.

BACKGROUND

Halocarbons containing fluorine (i.e., compounds containing only the elements carbon, fluorine, and optionally, chlorine and/or bromine) are widely used as refrigerants, aerosol propellants, blowing agents, cleaning agents, fire extinguishants and chemical intermediates. Commercially, many of such compounds are prepared by the reactions of hydrogen fluoride with olefins or saturated compounds containing chlorine. These processes can also produce halogenated hydrocarbons having a lesser commercial value and/or not having the desired properties. Furthermore, the supply/demand situation for any particular product can vary and there may be an oversupply of a particular halocarbon. For environmental reasons, it may not be advantageous to dispose of surplus or by-products by such methods as incineration, but rather to further react these materials to increase the yields of useful products. A reduction of the fluorine content of various halocarbons can improve their value as commercial products and/or as precursors for producing other useful products.

SUMMARY OF THE INVENTION

This invention provides a method for reducing the fluorine content of an acyclic saturated compound of the formula $C_nF_aX_b$ wherein each X is independently selected from Cl and Br, wherein n is 1 to 4, a is 2 to 10, b is 0 to 8, and a+b equals 2n+2, and wherein the acyclic saturated compound has at least one carbon with at least two fluorine substituents. The method comprises the step of reacting the acyclic saturated compound with HCl in the vapor phase at an elevated temperature in the presence of a catalyst, the mole ratio of HCl to the acyclic saturated compound being at least about 2:1.

DETAILED DESCRIPTION

The present invention provides a process for reducing the fluorine content of an acyclic saturated compound of the formula $C_nF_aX_b$ wherein each X is independently selected from Cl and Br, wherein n is 1 to 4, a is 2 to 10, b is 0 to 8, a+b equals 2n+2, and wherein the acyclic saturated compound has at least one carbon with at least two fluorine substituents, by reacting the acyclic saturated compound with HCl in the vapor phase in the presence of a catalyst. Examples include the reaction of $C_2Cl_2F_4$ (e.g., $CCl_2FCF_3$) with HCl (e.g., to form $CCl_3CF_3$); the reaction of $CCl_3CF_3$ with HCl to form $CCl_3CClF_2$; and the reaction of $C_3F_8$ with HCl to form chlorofluoropropanes (e.g., $C_3ClF_7$). The invention includes reactions of HCl with mixtures of compounds of the formula $C_nF_aX_b$ with each other and/or with other organic compounds such as ethers (e.g., dimethylether), alcohols (e.g., methanol) and hydrocarbons (e.g., propane and/or cyclohexane). In some embodiments, the mixtures are azeotropic. Examples of acyclic saturated compounds which may be reacted with HCl in accordance with this invention include $CCl_2F_2$, $CClF_3$, $CCl_2FCClF_2$, $CCl_3CF_3$, $CClF_2CClF_2$, $CClF_2CF_3$, $CCl_2FCF_3$, and $CBrF_3$.

The invention includes the reaction of HCl with compounds of the formula $C_nF_aX_b$ where n is at least 2 and b is at least 1. For some of these embodiments, the compound reacted with HCl can be prepared by isomerizing a thermodynamically less stable isomer. For example, $CClF_2CClF_2$ may first be isomerized to $CCl_2FCF_3$, which is then reacted with HCl to provide $CCl_3CF_3$. Also, $CCl_2FCClF_2$ may first be isomerized to $CCl_3CF_3$, which is then reacted with HCl to provide $CCl_3CClF_2$. Such isomerizations can be carried out prior to the reaction with HCl, but can also occur under reaction conditions.

Suitable catalysts which can be used for reducing the fluorine content of the starting materials by reaction with HCl include vapor phase fluorination catalysts. Catalysts which may be used in accordance with this invention include metals (including elemental metals, metal oxides and/or other metal salts) alumina; fluorided alumina; aluminum fluoride; metals on alumina; metals on aluminum fluoride; magnesium fluoride on aluminum fluoride; metals on fluorided alumina; alumina on carbon; aluminum fluoride on carbon; fluorided alumina on carbon; metals on carbon; chromium catalysts; mixtures of metals, aluminum fluoride, and graphite; and chromium-magnesium optionally on graphite. Suitable metals for use as catalysts (optionally on alumina, aluminium fluoride, fluorided alumina or carbon) include chromium, Group VIII metals (iron, cobalt, nickel, ruthenium, rhodium, palladium, osmium, iridium, platinum), Group VIIB metals (manganese, rhenium), Group IIIB metals (scandium, yttrium, lanthanum), Group IB metals (copper, silver, gold), zinc and/or metals having an atomic number of 58 through 71 (cerium, praseodymium, neodymium, promethium, samarium, europium, gadolonium, terbium, dysprosium, holmium, eribum, thulium, ytterbium or lutetium). Preferably, when used on a support, the total metal content of the catalyst will be from about 0.1 to 20 percent by weight; typically from about 0.1 to 10 percent by weight.

Fluorided alumina and aluminum fluoride can be prepared as described in U.S. Pat. No. 4,902,838. Metals on aluminum fluoride and metals on fluorided alumina can be prepared by procedures described in U.S. Pat. No. 4,766,260. Catalysts comprising chromium are well known in the art (see e.g., U.S. Pat. No. 5,036,036). Chromium supported on alumina can be prepared as described in U.S. Pat. No. 3,541,165. Chromium supported on carbon can be prepared as described in U.S. Pat. No. 3,632,834. Catalysts comprising chromium and magnesium may be prepared as described in Canadian Patent No. 2,025,145. Other metals and magnesium optionally on graphite can be prepared in a similar manner to the latter patent. Preferred catalysts include catalysts comprising aluminum fluoride and catalysts comprising chromium oxide.

The reaction of the acyclic saturated compound of the formula $C_nF_aX_b$ with HCl in the presence of the catalysts of the instant invention is suitably conducted at a temperature in the range of from about 250° C. to 550° C., preferably from about 300° C. to 500° C., and most preferably from about 325° C. to about 450° C.

The contact time is typically from about 1 to about 120 seconds, preferably from about 5 to about 60 seconds.

The amount of HCl should be at least a stoichiometric amount. Generally, the molar ratio of HCl to the acyclic saturated compound can range from about 2:1 to about 100:1, preferably about 3:1 to 50:1, and more preferably about 5:1 to 20:1.

In general, with a given catalyst composition, the higher the temperature and the longer the contact time, the greater is the conversion of fluorinated products and the greater is the production of polychlorinated products. The above variables can be balanced, one against the other, so that the formation of lower fluorine substituted products is maximized. For some embodiments it is preferred to react the acyclic compound of the formula $C_nF_aX_b$ to afford a compound with only one less fluorine atom.

The reaction products may normally be separated by conventional techniques, such as distillation. Some of the reaction products will have desired properties for commercial use by themselves, or as intermediates for making other commercial products. Others, such as $CCl_2=CCl_2$ can be recycled back to reactors which are being used for the synthesis of halofluorocarbons. The process of this invention provides a method of utilizing substantially all of a halogenated hydrocarbon plant's products. This utility has the benefit of providing a manufacturing facility with minimum waste, and therefore, minimum environmental impact.

The reaction of the acyclic saturated compound with HCl may be conducted in any suitable reactor, including fixed and fluidized bed reactors. The reaction vessel should be constructed from materials which are resistant to the corrosive effects of hydrogen fluoride such as Inconel TM nickel alloy and Hastelloy TM nickel alloy.

Pressure is not critical. Atmospheric and superatmospheric pressures are the most convenient and are therefore preferred.

Practice of the invention will become further apparent from the following non-limiting examples.

EXAMPLE 1

Reaction of HCl and $C_2Cl_2F_4$

A reactor (a 0.5 inch (1.3 cm) ID, 12 inch (30.5 cm) long Inconel TM nickel alloy pipe) was charged with 39.0 g (30 mL) of chrome oxide catalyst (10–20 mesh, 2.0 to 0.84 ram) and placed in a sand bath. The bath was gradually heated to 175° C. while $N_2$ gas at a flow rate of 50 cc/min was passed through the reactor to remove traces of water. After 4.5 hours, the nitrogen flow was stopped and HCl was passed through the reactor for 2.8 hours while gradually raising the reactor temperature to 400° C. At this point the temperature was reduced to 300° C. while passing HCl through the catalyst bed for an additional 55 minutes. Following this, the HCl flow was stopped and nitrogen passed over the catalyst overnight at 300° C. Thereafter, the nitrogen flow was stopped and the reactant flows were started. The $HCl:C_2Cl_2F_4$ molar ratio was varied from 2:1 to 20:1, the reaction temperature was varied from 300° to 375° C., and the contact time was 30 seconds. The results of these runs are shown in Table 1.

TABLE 1

| Hrs. on Stream | T °C. | Molar Ratio | % 115[a] | % 114[b] | % 114a[c] | % 113[d] | % 113a[e] | % 112/a[f] | % PCE[g] |
|---|---|---|---|---|---|---|---|---|---|
| 0 | 150 | Feed |  | 89.0 | 11.0 |  |  |  |  |
| 3 | 300 | 5:1 | 0.0 | 88.0 | 11.9 | 0.0 | 0.2 | 0.0 | 0.0 |
| 6 | 300 | 10:1 | 0.0 | 92.4 | 7.1 | 0.0 | 0.2 | 0.0 | 0.0 |
| 26 | 350 | 5:1 | 20.0 | 12.4 | 26.0 | 4.3 | 29.4 | 5.1 | 2.4 |
| 33 | 350 | 10:1 | 10.7 | 16.5 | 24.5 | 5.9 | 30.0 | 7.5 | 4.4 |
| 45 | 350 | 20:1 | 2.8 | 24.1 | 16.0 | 8.7 | 24.0 | 13.4 | 10.0 |
| 49 | 375 | 20:1 | 10.0 | 7.1 | 21.0 | 4.3 | 34.2 | 7.4 | 14.2 |

[a] 115 is $CClF_2CF_3$
[b] 114 is $CClF_2CClF_2$
[c] 114a is $CCl_2FCF_3$
[d] 113 is $CCl_2FCClF_2$
[e] 113a is $CCl_3CF_3$
[f] 112/a is $CCl_2FCCl_2F$ & $CCl_3CClF_2$
[g] PCE is $CCl_2=CCl_2$

EXAMPLE 2

Reaction of $C_2Cl_2F_4$ and HCl

A reactor (a 0.5 inch (1.3 cm) ID, 12 inch (30.5 cm) long Inconel TM nickel alloy pipe) was charged with 19.1 g (30 mL) of gamma-alumina and placed in a sand bath. The bath was gradually heated to 175° C. while $N_2$ gas at a flow rate of 50 cc/min was passed through the reactor to remove traces of water. After one hour, the nitrogen flow was stopped and HF was passed through the reactor for 4.5 hours. The reactor temperature was gradually raised to 400° C. over 4 hours while continuing to pass HF over the catalyst. At this point the temperature was reduced to 300° C., the HF stopped, and nitrogen flow started. After 5 minutes the nitrogen flow was reduced and HCl flow started. After another 5 minutes, the nitrogen flow was stopped and the flow of $C_2Cl_2F_4$ (about 90% $CClF_2CClF_2$) started.

The $HCl:C_2Cl_2F_4$ molar ratio was varied from 0.5:1 to 20:1, the reaction temperature was varied from 300° to 325° C. and the contact time was 30 seconds. The results of these runs are shown in Table 2.

TABLE 2

| Hrs. on Stream | T °C | Molar Ratio | % 115 | % 114 | % 114a | % 113 | % 113a | % 112/a | % PCE |
|---|---|---|---|---|---|---|---|---|---|
| 0 | 150 | Feed |  | 89.0 | 11.0 |  |  |  |  |
| 19 | 300 | 5:1 | 0.3 | 62.7 | 13.6 | 1.1 | 20.0 | 1.5 | 0.5 |
| 24 | 300 | 10:1 | 0.4 | 50.7 | 14.3 | 1.4 | 34.2 | 3.9 | 3.2 |
| 28 | 300 | 20:1 | 0.4 | 42.0 | 13.7 | 1.4 | 34.2 | 3.9 | 3.2 |

TABLE 2-continued

| Hrs. on Stream | T °C. | Molar Ratio | % 115 | % 114 | % 114a | % 113 | % 113a | % 112/a | % PCE |
|---|---|---|---|---|---|---|---|---|---|
| 44 | 325 | 5:1 | 1.9 | 32.8 | 30.0 | 1.6 | 30.9 | 1.7 | 0.8 |
| 50 | 325 | 20:1 | 2.0 | 14.8 | 23.5 | 2.2 | 46.3 | 4.7 | 5.1 |
| 56 | 325 | 2:1 | 2.0 | 40.0 | 34.0 | 1.1 | 21.5 | 0.8 | 0.3 |
| 61 | 325 | 0.5:1 | 2.7 | 44.5 | 40.1 | 0.7 | 11.8 | 0.20 | 0.0 |

EXAMPLE 3

Reaction of $C_2Cl_2F_4$ and $Cl_2$

The reactor and catalyst were the same as those used in Example 2. The $Cl_2:C_2Cl_2F_4$ molar ratio was as shown in Table 3, the reaction temperature was 200° C., and the contact time was 30 seconds. The results of these runs are shown in Table 3.

TABLE 3

| Hrs. on Stream | Molar Ratio | % 115 | % 114 | % 114a | % 113 | % 113a | % 112/a | % PCE |
|---|---|---|---|---|---|---|---|---|
| 0 | Feed |  | 89.0 | 11.0 |  |  |  |  |
| 92 | 0.1:1 | 15.4 | 10.7 | 57.9 | 0.2 | 15.7 | 0.0 | 0.0 |
| 95 | 0.5:1 | 12.9 | 14.0 | 59.5 | 0.2 | 13.4 | 0.0 | 0.0 |

EXAMPLE 4

Reaction of $CClF_2CF_3$ and $HCl$

The reactor and catalyst was the same as that used in Example 2. The $HCl:CClF_2CF_3$ (CFC-115) molar ratios and reaction temperatures were as shown Table 4, and the contact time was 30 seconds. The results of these runs are shown in Table 4.

TABLE 4

| Hrs. on Stream | T °C. | Molar Ratio | % 115 | % 114 | % 114a | % 113 | % 113a | % 112/a | % PCE |
|---|---|---|---|---|---|---|---|---|---|
| 2 | 275 | 10:1 | 95.5 | 0.1 | 0.3 | 0.1 | 2.1 | 0.4 | 1.3 |
| 6 | 375 | 10:1 | 66.7 | 1.3 | 10.3 | 0.9 | 13.6 | 1.5 | 4.6 |
| 8 | 375 | 5:1 | 75.5 | 1.3 | 9.7 | 0.6 | 9.7 | 0.8 | 1.8 |
| 12 | 400 | 20:1 | 44.1 | 2.1 | 13.7 | 1.6 | 19.4 | 2.6 | 13.7 |

EXAMPLE 5

Reaction of HCl and $CCl_2F_2$

A reactor (a 0.5 inch (1.3 cm) ID, 12 inch (30.5 cm) long Inconel ™ nickel alloy pipe) was charged with 23.6 g (30 mL) of aluminum fluoride and placed in a sand bath. The bath was gradually heated to 176° C. while $N_2$ gas at a flow rate of 50 cc/min was passed through the reactor. After 28 minutes, the nitrogen flow was stopped and HF was passed through the reactor for 2.0 hours while gradually raising the reactor temperature to 401° C. At this point the temperature was reduced to 280° C. while passing HF through the catalyst bed for an additional 55 minutes. Following this, the HF flow was stopped and nitrogen passed over the catalyst until the temperature was 200° C. Thereafter, the nitrogen flow was stopped and the reactant flows were started.

The $HCl:CCl_2F_2$ (CFC-12) molar ratio was 20:1, the reaction temperature was varied from 200° to 275° C. and the contact time was 30 seconds. The results of these runs are shown in Table 5.

TABLE 5

| Hrs. on Stream | T °C. | % 13[a] | % 12[b] | % 11[c] | % 20[d] | % 10[e] |
|---|---|---|---|---|---|---|
| 2 | 200 | 0.0 | 97.9 | 0.0 | 0.2 | 1.2 |
| 15 | 250 | 20.0 | 63.7 | 4.7 | 0.2 | 11.3 |
| 8 | 275 | 52.7 | 3.9 | 0.1 | 0.5 | 42.6 |

[a]13 is $CClF_3$
[b]12 is $CCl_2F_2$
[c]11 is $CCl_3F$
[d]20 is $CHCl_3$
[e]10 is $CCl_4$

EXAMPLE 6

Reaction of HCl and $C_2Cl_2F_4$

A. Catalyst Preparation

Samples of powdered gamma-alumina and graphite were dried overnight at 110° C. The dried, powdered gamma-alumina (100 g) was mixed with the dried graphite (96 g). A solution containing $ZnCl_2$ (4.6 g) in water (175 mL) was added to the mixture. The mixture was kneaded well after an additional 20 mL of water was added After drying overnight at 100° C. the sample was granulated to 20/40 mesh (0.84/0.42 mm). Chemical analysis showed a Zn/Al ratio of 0.016. The surface area was 116 m²/g as measured by nitrogen adsorption.

B. Catalyst Activation and Reaction

The reactor (a 0.5 inch (1.3 cm) ID, 12 inch (30.5 cm) long Inconel ™ nickel alloy pipe) was charged with 13.6 g (30 mL) of $Zn-Al_2O_3$/graphite catalyst and placed in a sand bath. The bath was gradually heated to about 400° C. while $N_2$ gas at a flow rate of 50 cc/min. was passed through the reactor for about 2.5 hrs. The catalyst bed was then cooled under nitrogen over 1.5 hours to about 175° C. At that time in addition to nitrogen, HF was passed through the catalyst bed at 50 cc/min. After a few minutes at these conditions, a temperature rise to about 200° C. was observed. After an hour the temperature had decreased to about 175° C. whereupon the nitrogen flow was reduced to 20 cc/min. and the HF flow increased to 80 cc/min. Over 2.5 hours the bath temperature was gradually increased to about 340° C. At this point an increase in the catalyst bed temperature to 372° C. was observed. During the next 0.75 hour the bath temperature was gradually increased to 390° C. with the catalyst bed temperature rising to 411° C. At this point the nitrogen flow was increased to 75 cc/min. and the HF flow decreased to 25 cc/min. During the next 0.75 hour the flows were gradually adjusted to 15 cc/min nitrogen and 80 cc/min. HF and both the bath and catalyst temperature were about 400° C. Following this, the HF flow was stopped and nitrogen passed over the catalyst until the temperature was 300° C. Thereafter, the nitrogen flow was stopped and the reactant flows started. The HCl:C$_2$Cl$_2$F$_4$ molar ratio was 20:1, the reaction temperature was varied from 300° to 350° C. and the contact time was 30 seconds The results of these runs are shown in Table 6.

TABLE 6

| Hrs. on Stream | T °C. | % 115 | % 114 | % 114a | % 113 | % 113a | % 112/a | % 111[a] | % PCE |
|---|---|---|---|---|---|---|---|---|---|
| 0 | 150 | | 87.6 | 12.0 | | | | | |
| 2 | 300 | 0.1 | 76.6 | 3.1 | 1.3 | 10.6 | 4.1 | 0.6 | 3.1 |
| 5 | 325 | 0.3 | 58.7 | 7.2 | 3.0 | 16.2 | 6.8 | 0.7 | 6.3 |
| 9 | 350 | 8.3 | 6.8 | 24.1 | 2.9 | 42.8 | 5.5 | 0.5 | 7.9 |

[a]111 is CCl$_3$CCl$_2$F

EXAMPLE 7

Reaction of HCl and CF$_3$Br

A reactor (a 0.5 inch (1.3 cm) ID, 12 inch (30.5 cm) long Inconel TM nickel alloy pipe) was charged with 23.5 g (30 mL) of aluminum fluoride and placed in a sand bath. The bath was gradually heated to about 180° C. while N$_2$ gas at a flow rate of 50 cc/min was passed through the reactor. After a ½ hour, the nitrogen flow was stopped and HF was passed through the reactor for 2 hours while gradually raising the reactor temperature to about 400° C. At this point the temperature was reduced to 280° C. while passing HF through the catalyst bed for an additional hour. Following this, the HF flow was stopped and nitrogen passed over the catalyst until the temperature was 200° C. Thereafter, the nitrogen flow was stopped and the reactant flows were started.

The HCl:CF$_3$Br (FC-13B1) molar ratio was 20:1, the reaction temperature was varied from 300° to 400° C. and the contact time was 30 seconds. The results of these runs are shown in Table 7.

EXAMPLE 8

Reaction of HCl and CF$_3$CF$_2$CF$_3$

A reactor (a 0.25 inch (0.65 cm) O.D. by 10 cm long Inconel TM nickel alloy pipe with a wall thickness of 0.035 inch (0.9 mm)) was charged with 2.0 g (1.5 mL) of chrome oxide catalyst (14–20 mesh, 1.4 to 0.84 mm) and placed in a sand bath. The bath was gradually heated to 400° C. while N$_2$ gas at a flow rate of 50 cc/minute was passed through the reactor to remove traces of water. After 4.5 hours, the nitrogen flow was stopped and HCl was passed through the reactor for about 20 minutes while gradually raising the reactor temperature to 500° C. CF$_3$CF$_2$CF$_3$ was fed to the reactor. The HCl:C$_3$F$_8$ (FC-218) molar ratio was about 33:2, the reaction temperature was about 500° C. The FC-218 conversion was 12.2% to chlorofluoropropanes.

It is understood that the invention is not confined to the particular formulations and examples herein illustrated, but it embraces such modified forms thereof as come within the scope of the following claims.

What is claimed is:

1. A method for reducing the fluorine content of an acyclic saturated compound of the formula C$_n$F$_a$X$_b$ wherein each X is independently selected from the group consisting of chlorine and bromine, wherein n is 1 to 4, a is 2 to 10, b is 0 to 8, and a+b equals 2n+2, and wherein the acyclic saturated compound has at least one carbon with at least two fluorine substituents, comprising the step of:
   reacting said acyclic saturated compound with HCl in the vapor phase at a temperature in the range of from about 250° C. to 550° C. in the presence of a catalyst, the mole ratio of HCl to said acyclic saturated compound being at least about 2:1.

2. The method of claim 1 wherein the catalyst comprises aluminum fluoride.

3. The method of claim 1 wherein the catalyst comprises chromium oxide.

4. The method of claim 1 wherein the catalyst is selected from alumina, fluorided alumina, magnesium fluoride on aluminum fluoride, alumina on carbon, alu-

TABLE 7

| Hrs. on Stream | T °C. | % 23[a] | % 13 | % 13B1[b] | % 12 | % 12B1[c] | % 11 | % 20 | 10% | % other[d] |
|---|---|---|---|---|---|---|---|---|---|---|
| 5 | 325 | 0.0 | 0.1 | 99.7 | 0.0 | 0.1 | 0.0 | 0.0 | 0.0 | 0.1 |
| 10 | 350 | 0.2 | 89.6 | 9.3 | 0.5 | 0.1 | 0.0 | 0.0 | 0.0 | 0.3 |
| 15 | 350 | 0.5 | 82.6 | 9.4 | 4.0 | 1.1 | 0.3 | 0.8 | 0.7 | 0.7 |
| 19 | 375 | 0.9 | 82.3 | 8.2 | 4.3 | 1.2 | 0.4 | 1.3 | 0.7 | 0.7 |
| 20 | 400 | 1.2 | 82.9 | 7.6 | 4.3 | 1.2 | 0.4 | 1.2 | 0.6 | 0.7 |
| 25 | 300 | 0.1 | 36.5 | 50.6 | 9.4 | 1.0 | 0.7 | 0.1 | 1.5 | 0.2 |
| 26 | 325 | 0.1 | 75.0 | 12.9 | 6.7 | 1.0 | 0.6 | 0.5 | 1.9 | 0.9 |
| 27 | 350 | 0.2 | 83.3 | 4.6 | 6.1 | 1.0 | 0.7 | 1.2 | 2.2 | 0.9 |
| 28 | 375 | 0.4 | 82.2 | 4.0 | 6.5 | 1.1 | 0.7 | 2.0 | 2.3 | 0.9 |

[a]23 is CHF$_3$
[b]13B1 is CBrF$_3$
[c]12B1 is CBrClF$_2$
[d]includes CHClF$_2$ and CHCl$_2$F minum fluoride on carbon and fluorided alumina on carbon.

5. The method of claim 1 wherein the catalyst comprises a metal selected from the group consisting of chromium, zinc, Group VIII metals, Group VIIB metals, Group IIIB metals, Group IB metals, and metals having an atomic number of 58 through 71.

6. The method of claim 5 wherein the metal is on alumina, aluminum fluoride, fluorided alumina on carbon; and wherein the total metal content is from about 0.1 to 20 percent by weight.

7. The method of claim 1 wherein a compound with only one less fluorine is produced.

8. The method of claim 1 wherein the compound $CCl_2FCF_3$ is reacted with HCl to provide $CCl_3CF_3$, and is prepared by isomerizing $CClF_2CClF_2$.

9. The method of claim 1 wherein the acyclic saturated compound is selected from the group consisting of $CCl_2CF_2$, $CClF_3$, $CCl_2FCClF_2$, $CCl_3CF_3$, $CClF_2CClF_2$, $CClF_2CF_3$, $CCl_2FCF_3$, and $CBrF_3$.

10. The method of claim 1 wherein n is at least 2 and b is at least one.

11. The method of claim 1 wherein $C_2Cl_2F_4$ is reacted with HCl.

12. The method of claim 1 wherein the compound $CCl_3CF_3$ is reacted with HCl to provide $CCl_3CClF_2$, and is prepared by isomerizing $CCl_2FCClF_2$.

13. A process for reducing the fluorine content of a chlorofluoroethane consisting of carbon, chlorine and fluorine and having at least one carbon with at least two fluorine substituents, comprising the steps of:

reacting said chlorofluoroethane with a fluorine-reducing reagent consisting essentially of HCl in the vapor phase at a temperature in the range of from about 300° C. to 450° C. in the presence of a catalyst comprising aluminum fluoride to produce $Cl_2C=CCl_2$, the mole ratio of HCl to said chlorofluoroethane being at least about 5:1.

14. The process of claim 13 wherein the chlorofluoroethane is a dichlorotetrafluoroethane.

15. The process of claim 13 wherein the chlorofluoroethane is a trichlorotrifluoroethane.

16. The process of claim 13 wherein the chlorofluoroethane is chloropentafluoroethane.

17. A process for reducing the fluorine content of an acyclic saturated compound of the formula $C_nF_a$ wherein n is 1 to 4, and a equals 2n+2 comprising the step of:

reacting said acyclic saturated compound with HCl in the vapor phase at a temperature in the range of from about 250° to 550° C. in the presence of a chromium oxide catalyst, the mole ratio of HCl to said acyclic saturated compound being at least about 5:1.

18. The process of claim 17 wherein the acyclic saturated compound is $CF_3CF_2CF_3$.

19. The process of claim 18 wherein the reaction temperature is about 500° C. and a 12.2% conversion to chlorofluoropropanes is reached.

20. The method of claim 1 wherein said acyclic saturated compound is reacted with a fluorine-reducing reagent consisting essentially of said HCl.

* * * * *